United States Patent [19]

Le Caire, Jr. et al.

[11] 4,372,490

[45] Feb. 8, 1983

[54] PULL PAD CONCENTRATED AIR DEODORIZER

[75] Inventors: Robert A. Le Caire, Jr., Appleton; David W. Wendt, Madison, both of Wis.

[73] Assignee: The Coca-Cola Company, Atlanta, Ga.

[21] Appl. No.: 208,574

[22] Filed: Nov. 20, 1980

[51] Int. Cl.³ .............................................. A61L 9/00
[52] U.S. Cl. ................................... 239/59; 220/4 E; 220/302
[58] Field of Search ................................... 239/57–60; 206/0.5; 220/4 E, 4 B, 8, 302; D23/150

[56] References Cited

U.S. PATENT DOCUMENTS

| D. 162,679 | 3/1951 | Munnecke | D23/150 |
| 3,908,906 | 9/1975 | Crowle et al. | 239/58 |
| 4,014,501 | 3/1977 | Buckenmayer | 239/58 |

FOREIGN PATENT DOCUMENTS 1074246 10/1954 France .............................. 220/4 B

*Primary Examiner*—Andres Kashnikow
*Attorney, Agent, or Firm*—Birch, Stewart, Kolasch & Birch

[57] ABSTRACT

The present invention is directed to a deodorant container in which an air-treating material is positioned. The air-treating material can be either a volatile material or a material which absorbs odors. The container includes a top member movable mounted within a base member. The top member and the base member are identical in shape and may be formed from a common mold. The air-treating material is in the form of a disk which is disposed between the top member and the base member. The top member and the base member include outwardly projecting engaging legs including detents disposed on the outer surface thereof. These legs are spaced to provide air passages therebetween. The detents mate with corresponding engaging slots disposed in the side wall construction of the corresponding top or base member. In a closed position wherein the top and base members are fully nested within each other, the detents engage a cam slot which locks the top member relative to the base member to seal the container. To open the container, the top member is slightly rotated relative to the base member only to unlock the two members. Thereafter, the top member is reciprocated relative to the base member to open the container and thereby expose the air-treating material through the air passages between the engaging legs. The engaging legs of the top member include inwardly projecting disk centering tabs which raise the air-treating disk upwardly, as the container is opened, to center the disk with respect to the air passages formed between the top member and the base member.

39 Claims, 12 Drawing Figures

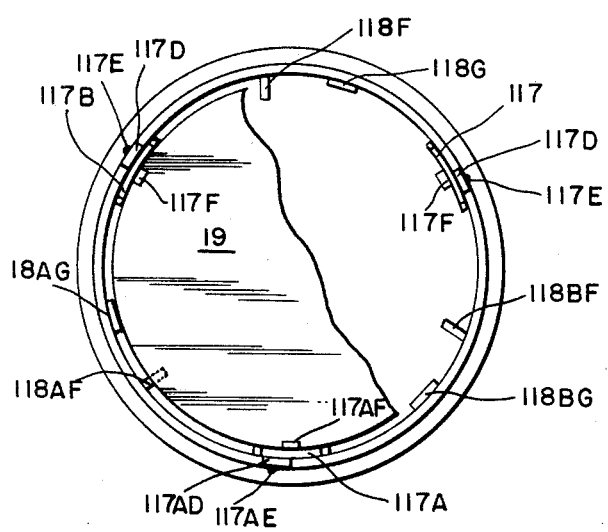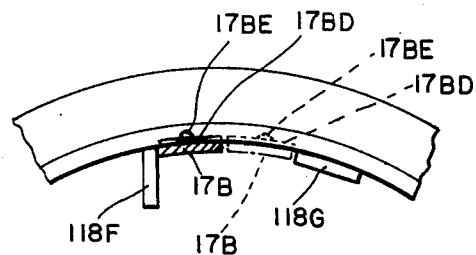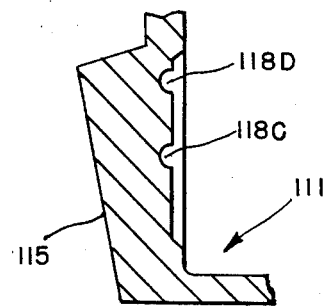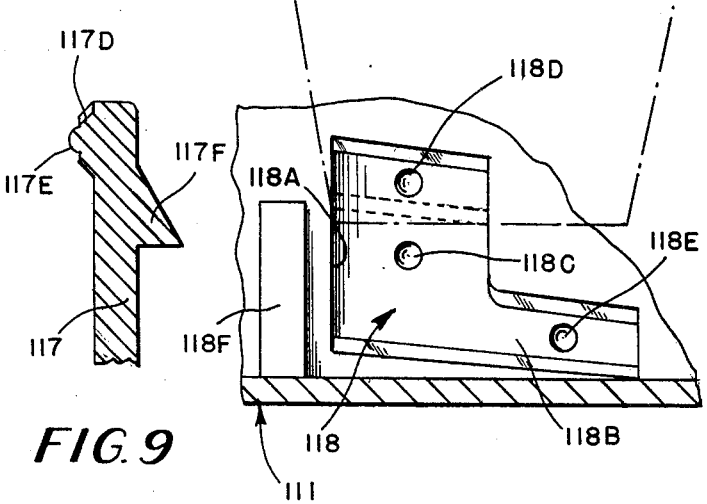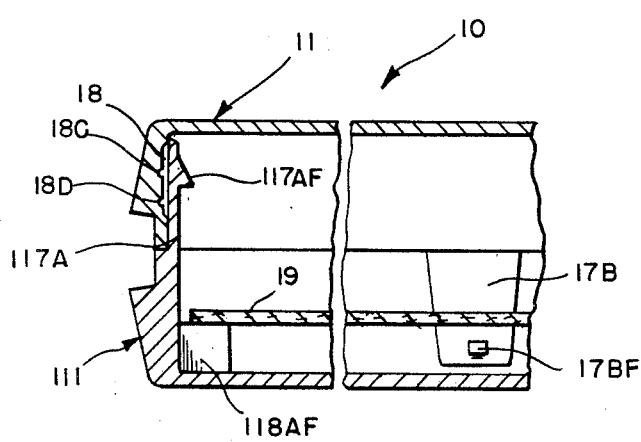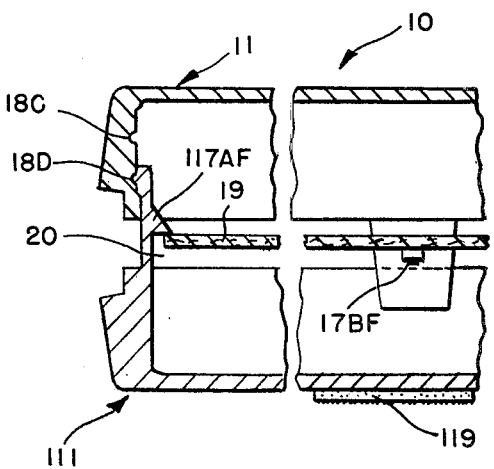

PULL PAD CONCENTRATED AIR DEODORIZER

BACKGROUND OF THE INVENTION

1. Field of the Invention

The present invention relates to a deodorant container wherein a top member and a base member are formed as identical units from a common mold. The top member and the base member are designed to be affixed relative to each other to form a space therebetween. The space between the top member and the base member is designed to receive a disk of air-treating material. In a locked position, the top member is firmly secured relative to the base member so that the air-treating material is sealed therebetween. In an open position, the top member is slightly rotated to unlock it relative to the base member and thereafter is reciprocated upwardly to expose the disk or air-treating material to the ambient air.

2. Description of the Prior Art

In the past, it has been conventional to dispense a deodorant material by positioning a wick within a liquid deodorant disposed within a container. The wick would tend to draw the liquid deodorant upwardly out of the container thereby pemitting it to permeate the surrounding ambient air. With this type of conventional room deodorant the container is open and the contents of the container may be accidentally spilled. In addition, this conventional type of room deodorant is extremely messy since the wick must be manually removed from the liquid deodorant positioned within the container.

To overcome the deficiencies of the conventional liquid deodorant container, a number of devices have been developed whereby the contents of the container may be sealed off from the ambient air and thereafter opened to expose the contents to the ambient air. For example, the Dupuy Patent, U.S. No. 2,383,960 discloses a vaporizing device wherein a wick 14 is disposed within a liquid deodorant 12 positioned within a container 10. At the uppermost end of the container is a closure member 26, 37 which may be rotated to either expose the contents of the container to the ambient air or to seal off the contents of the container from the ambient air. Although this device apparently eliminates the mess accompanying manually removing the wick from the liquid deodorant positioned within the container, it still suffers from a disadvantage in that if the container is accidentally dislodged, the contents of the container may be spilled. Another device which is extremely similar to the Dupuy '960 Patent is the Dupuy Patent, U.S. No. 2,412,326. Again, the Dupuy '326 Patent suffers from the same disadvantages as the Dupuy '960 Patent.

A number of dispensing devices have been developed whereby a solid or particulate deodorant material is positioned within a container. For example, the Logue Patent, U.S. No. 2,555,047; Wheeler et al Patent, U.S. No. 2,603,532; Meek Patent, U.S. No. 2,657,090; the Wenner Patent, U.S. No. 2,836,462; and the Buckenmayer Patent, U.S. No. 4,014,501, all disclose containers whereby a top member is rotatably positioned on a bottom member. By rotating the top member relative to the bottom member either one or a plurality of apertures are opened thereby exposing the contents of the container to the ambient air. Although these devices overcome some of the deficiencies of the prior art room deodorizers, they suffer from a construction disadvantage in that the top member has a different configuration from the base member. In other words, to construct the container, it is necessary to mold the top member in a completely distinct mold from that used to mold the bottom member. This greatly increases the expense involved with constructing the container. In addition, it is necessary to closely monitor the construction of the top members and the base members to make sure that an equal quantity of members are being manufactured.

Similarly, the Wheeler Patent, U.S. No. 2,765,951; the Copley Patent, U.S. No. 3,134,544; and the Burdick Patent, U.S. No. 3,286,872, all disclose containers wherein a deodorant material is positioned in a base member and a top member is reciprocated upwardly to expose the contents of the base member to the ambient air. Both the Wheeler and Burdick Patents disclose a top member which is of a different construction than the bottom member. Therefore, it is necessary to use a first mold to construct the top member and a second distinct mold to construct the bottom member.

The Copley Patent discloses one embodiment wherein the cover 28 is molded in the same die as the container 11. However, it is necessary to employ a retaining sleeve 21 having an outwardly projecting conical surface 26 in order to secure the cover member 28 relative to the container member 11. In addition, during operation, the cover member 28 is removed from the container member 11 and is stored adjacent the lower end of the container member 11 forming a base therefor.

SUMMARY OF THE INVENTION

Accordingly, it is a primary object of the present invention to provide a container wherein the top member and the base member are identical elements constructed from a single mold.

Another object of the present invention is to provide a container wherein the top member and the base member may be interconnected to each other to form an operative container which may be sealed or opened.

A still further object of the present invention is to provide a container wherein a disk of air-treating material is disposed between a top member and a base member, the disk of air-treating material being operatively connected to disk centering tabs within the top member and the base member whereby opening the top member relative to the base member laterally moves the disk of air-treating material relative to the base member, so that the disk is centered with respect to air passages formed between the top member and the base member.

A further object of the present invention is to provide a top member and a base member which include outwardly projecting engaging legs which mate with engaging slots in the side wall of the base member and top member, respectively, so that the top member may be reciprocated outwardly from the base member thereby defining air passages therebetween, said engaging legs indexing in the engaging slots so as to adjust said top member relative to said base member in a plurality of various positions to define different size air passages.

A still further object of the present invention is to provide a cam slot adjacent to the engaging slot so that after the top member is closed relative to the base member, the camming slot permits the top member to be locked relative to the base member.

These and other objects have been fulfilled in the present invention by providing a top member which is constructed in an identical configuration to the base member. The top member includes three downwardly projecting engaging legs which are adapted to be received within three engaging slots positioned on the interior surface of the base member. Similarly, the base member which is identical to the top member, includes three upwardly projecting engaging legs designed to mate with three engaging slots formed on the interior surface of the top member. The engaging legs of each respective member are spaced defining air passages therebetween when the container is open. A disk of air-treating material is positioned between the top member and the base member and is normally positioned within the base member when the container is sealed. In the open position, the top member is slightly rotated relative to the base member to disengage the engaging legs of both the top member and the base member from corresponding cam slots. Thereafter, the top member is reciprocated upwardly relative to the base member whereby detents positioned on the engaging legs of both the top member and the base member are received within indexing recesses disposed in the engaging slots positioned on the inner surface of the top member and the base member. As the top member is reciprocated upwardly relative to the base member, disk centering tabs raise the disk of air-treating material upwardly thereby centering the disk with respect to air passages defined by the spaces between the engaging legs.

BRIEF DESCRIPTION OF THE DRAWINGS

The objects of the present invention and the attendant advantages thereof will become more readily apparent by reference to the following drawings wherein:

FIG. 6 is a top view of the deodorant container as illustrated in FIG. 4;

FIG. 7 is an enlarged view illustrating in solid lines, an engaging leg according to the present invention disposed within an engaging slot and in dotted lines, an engaging leg disposed within a cam slot in the container locked position;

FIG. 8 is a partial cross-sectional view, taken along line 8—8 of FIG. 4, and illustrating the construction of the engaging slot which includes at least two recesses for positioning a detent therein;

FIG. 9 is an enlarged cross-sectional view, taken along line 9—9 of FIG. 5, and illustrating the construction of an engaging leg with a cam block and detent projecting outwardly therefrom and a disk centering tab disposed on the inner portion thereof;

FIG. 10 is an enlarged cross-sectional view illustrating in solid lines the engaging slot and cam slot and in dotted lines an engaging leg disposed within the recess positioned adjacent the upper portion of the engaging slot;

FIG. 11 is a cross-sectional view of the deodorant container illustrated in FIG. 1 showing the deodorant container in the closed position; and FIG. 12 is a cross-sectional view of the deodorant container illustrated in FIG. 2 showing the deodorant container in an open position and the disk of air-treating material centered within an aperture formed between the top member and the base member.

DETAILED DESCRIPTION OF THE PREFERRED EMBODIMENTS

Figure 1:
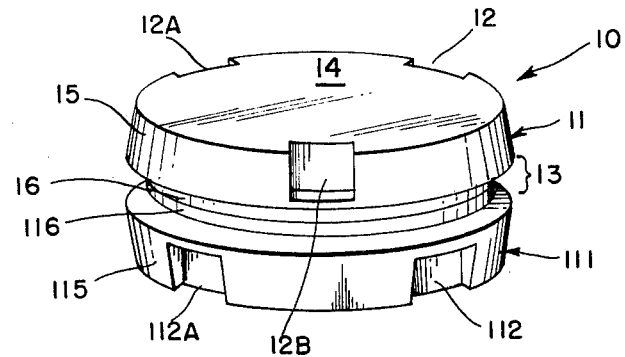
FIG. 1 is a side perspective view illustrating the deodorant container according to the present invention in a closed position.

Referring in detail to FIG. 1, there is illustrated a deodorant container 10 shown in the closed position. The deodorant container 10 includes a top member or housing section 11 which is identical in construction to a base member or housing section 111. The top member 11 includes a flat upper surface 14 and a sloped side wall 15. The sloped side wall 15 includes decorative notches 12, 12A, and 12B. Similarly, the base member 111 includes a sloped side wall 115 having decorative notches 112, 112A, and 112B (not illustrated in the drawings).

As shown in FIG. 1, the top member 11 includes the sloped side wall 15 including a lower indented portion which forms a sealing ridge 16. Similarly, the base member 111 includes a sloped side wall 115 including an upper indented portion which forms a sealing ridge 116. The indented portions formed between the sloped side walls 15, 115 and the sealing ridges 16, 116 form an indentation 13. As discussed hereinbelow, the deodorant container 10 has two closed positions, namely, a releasably locked closed position and an unlocked closed position.

Figure 2:
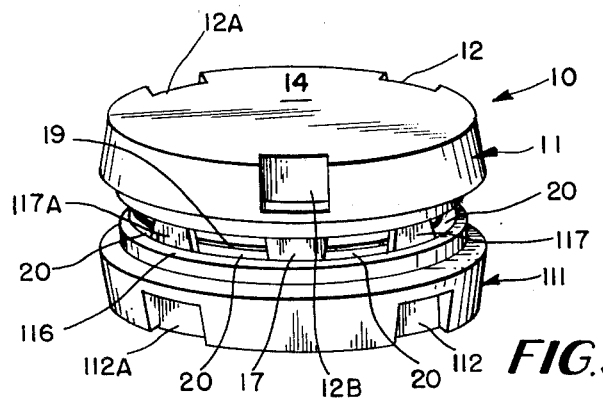
FIG. 2 is a side perspective view of the deodorant container according to the present invention illustrating the container in an open position.

Referring in detail to FIG. 2, the deodorant container 10 is illustrated in the open position. Like numerals in FIG. 2 represent the same elements as previously discussed with respect to FIG. 1. In the open position the sealing ridge 116 is shown to have a predetermined thickness which mates with a corresponding, identical thickness of the sealing ridge 16 of the top member 11. When the top member 11 is reciprocated upwardly relative to the base member 111, a plurality of spaced engaging legs define air passages 20 between the top member 11 and the base member 111. As illustrated in FIG. 2, the top member 11 includes an outwardly projecting engaging legs 17. Similarly, the base member 111 includes outwardly projecting engaging legs 117 and 117A. It is to be understood, that the top member 11 and the base member 111 each include three outwardly projecting engaging legs spaced 120° apart. The leg acts as indexing members. However, all of the outwardly projecting engaging legs are not illustrated in the side perspective view of FIG. 2. When the top member and the base member are nested relative to each other, the outwardly projecting engaging legs of the top member are positioned between the outwardly projecting engaging legs of the base member and are thus spaced 60° apart relative to each other. When the top and base members are closed, the legs of the top member telescope into the base member, similarly, the legs of the base member telescope into the top member.

As the top member 11 is reciprocated upwardly relative to the base member 111, a disk 19 of air-treating material is raised upwardly in a manner to be described more fully hereinafter. As illustrated in FIG. 2, the disk 19 of air-treating material is centered in the air passages defined by the engaging legs of the top member 11 and the base member 111.

Figure 3:
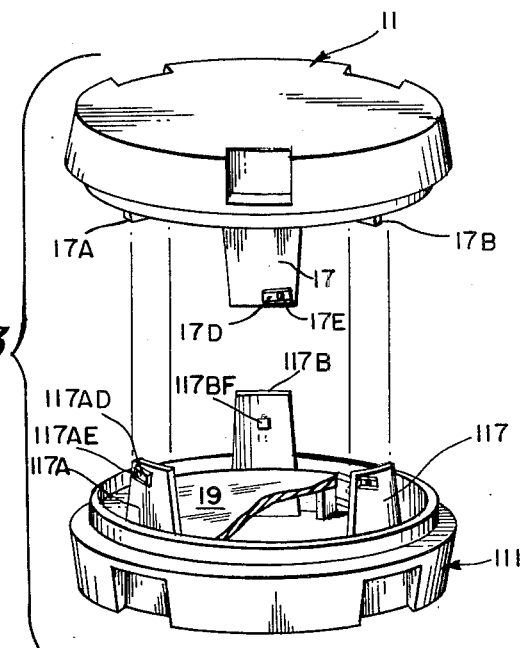
FIG. 3 is an exploded view of the deodorant container according to the present invention illustrating the top member in a position which is completely detached from the base member and illustrating a partial cutaway view of the disk of air-treating material positioned within the base member.
Figure 4:
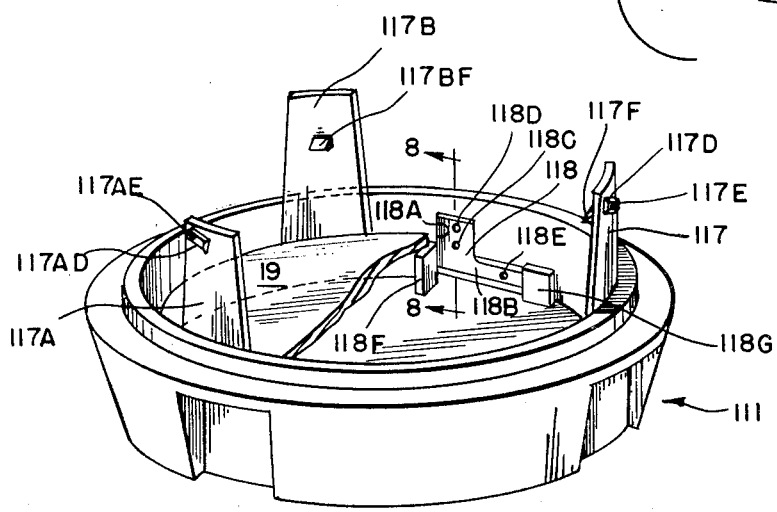
FIG. 4 is an enlarged view of the base member of the deodorant container according to the present invention illustrating a partial cutaway section of the disk of air-treating material thereby exposing one of three engaging slots disposed around the inner surface of the base member.

Referring in detail to FIGS. 3 and 4, the deodorant container 10 is illustrated in a detached position whereby the top member 11 is removed from the base member 111 to illustrate the internal construction of the respective members. As illustrated in FIGS. 3 and 4, the base member 111 includes three upwardly projecting engaging legs 117, 117A, and 117B. The projecting engaging legs 117, 117A, and 117B are spaced at approximately 120° with respect to each other. Similarly, the top member 11 includes downwardly projecting engaging legs 17, 17A, and 17B. As previously discussed, the top member 11 is identical in construction to the base member 111. Therefore, both the top member 11 and the base member 111 may be constructed from the same mold.

Figure 5:
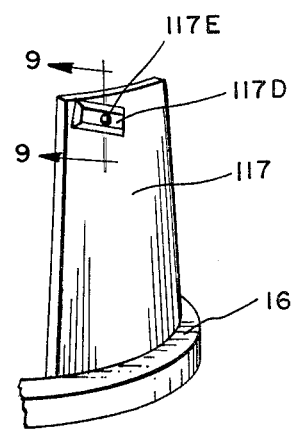
FIG. 5 is an enlarged view of an external surface of an engaging leg of the present invention.

Each outwardly projecting engaging leg includes on an outwardly facing surface a cam block and a detent thereon. As illustrated in FIGS. 3, 4, 5, 6, and 9, the outwardly projecting engaging leg 117 includes a cam block 117D and detent 117E. Similarly, the outwardly projecting engaging leg 17 includes a cam block 17D and a detent 17E. Further, the outwardly projecting engaging leg 117A includes a cam block 117AD and a detent 117AE. As illustrated in FIGS. 3, 4, and 5 the cam blocks 117D, 117AD, and 17D are canted at an angle on the respective outwardly projecting engaging leg on which they are disposed for reasons to be explained hereinafter. In addition, each of the outwardly projecting legs includes a disk centering tab on an inner surface thereof (FIG. 6). As illustrated in FIGS. 3, 4, 6, and 9, the outwardly projecting engaging leg 117 includes a disk centering tab 117F. Similarly, the outwardly projecting engaging leg 117B includes a disk centering tab 117BF and the leg 117A includes a disk centering tab 117AF.

Referring to FIGS. 3, 4, and 8 to 10, the base member 111 includes a plurality of engaging slots 118 formed on the inside of side wall 15. The engaging slots 118 include a vertical portion 118A and a cam slot portion 118B. Further, the vertical portion 118A includes indexing recesses 118C and 118D which are designed to mate with the detents of outwardly projecting engaging legs of the top member 11. Similarly, the cam slot 118B includes a locking recess 118E which is designed to mate with detents of outwardly projecting engaging legs of the top member 11. Positioned adjacent to engaging slots 118 is a stop and disk support 118F which is designed to support the disk of air-treating material 19 and to prevent the dislodging of the cam blocks and detents of an outwardly projecting engaging leg of the top member 11 from within the engaging slot 118. In addition, the cam slot 118B includes a lock rib 118G at the opposite end which prevents corresponding cam blocks and detents of outwardly projecting legs of the top member 11 from becoming dislodged from the cam slot 118B at said opposite end. Disposed around the internal side walls of both the base member 111 and the top member 11 are three engaging slots 118 spaced at approximately 120° with respect to each other. The engaging slots are specifically designed to mate with corresponding outwardly projecting engaging legs of the top member or base member, respectively.

As best illustrated in FIG. 6, the interior circumference of the base member 111 is provided with three spaced stop and disk supports 118F, 118AF, and 118BF. In addition, disposed around the interior circumference of the base member 111 are three locking ribs 118G, 118AG, and 118BG. Disposed adjacent to the outwardly projecting engaging legs 117, 117A, and 117B, are the associated engaging slots and cam slots which are disposed within the thickness of the sloped wall 115 and are visible in FIG. 6.

As illustrated in FIG. 7, the base member 111 includes a stop and disk support 118F and a locking rib 118G. As shown in solid lines, an outwardly projecting engaging leg 17B is disposed adjacent to a corresponding engaging slot 118, not illustrated in FIG. 7, to secure the top member 11 to the base member 111. The outwardly projecting engaging leg 17B includes a cam block 17BD and detent 17BE. As illustrated in dotted lines, the outwardly projecting engaging leg 17B is disposed within the cam slot 118B, not illustrated in FIG. 7.

Referring to FIG. 11, the deodorant container 10 is illustrated in the closed position. In this position the top member 11 is sealed to the base member 111. The disk of air-treating material 19 is disposed on the stop and disk support 118AF and the two additional stop and disk supports, not illustrated in FIG. 11. The top member 11 includes an engaging slot 18 having two recesses 18C and 18D. In addition, the top member 11 includes an outwardly projecting engaging leg 17B having a disk and centering tab 17BF.

In the closed position the outwardly projecting engaging legs 17, 17A, and 17B of the top member 11 and the outwardly projecting engaging legs 117, 117A, and 117B of the base member 111 are telescoped within the corresponding engaging slots of the base member 111 and the top member 11, respectively. In addition, in the closed and locked position the outwardly projecting engaging legs 17, 17A, and 17B of the top member 11 and the outwardly projecting engaging legs 117, 117A, and 117B of the base member 11 are positioned within a corresponding cam slot of the base member 111 and the top member 11, respectively. In the closed position the disk and centering tabs which are disposed on each of the outwardly projecting legs 17, 17A, and 17B of the top member 11 and on each of the outwardly projecting legs 117, 117A, and 117B of the base member 111 are out of engagement with the disk 19 of air-treating material.

As illustrated in FIG. 12, in the fully open position the disk centering tab 17BF is in engagement with the disk 19 and causes it to be reciprocated upwardly to center the disk 19 within the air passages 20 formed between the top member 11 and the base member 111. The two additional disk centering tabs positioned on the outwardly projecting legs 17 and 17A also aid in the positioning of the disk 19 of air-treating material.

FIG. 12 illustrates the deodorant container 10 in the fully opened position. It is to be understood, that by positioning the detents on the outwardly projecting legs in the respective indexing recesses provided within the corresponding engaging slots will provide adjustable degrees of opening for the deodorant container 10. That is, the size of the air passages 20 between the engaging legs may be varied. It is only in the fully opened position that the disk 19 is centered within the air passages 20.

In operation, the container is originally closed whereby the cam blocks and detents of the outwardly projecting engaging legs are disposed within corresponding cam slots. In this position, the container is locked. If one desires to open the deodorant container 10, one merely slightly rotates the top member 11 relative to the base member 111 to unlock the container. Following rotation the container is still closed. Thereafter, by reciprocating the top member 11 relative to the base member 111, the container is opened providing air passages 20 between the top member 11 and the base member 111. The disk center tabs raise the disk 19 of air-treating material to a position wherein the disk 19 is centered relative to the aperture provided between the top member 11 and the base member 111. In the open condition, the container is activated to treat the air within the room in which it is positioned. The deodorant container 10 may be positioned on a horizontal surface or a protective covering may be removed from the adhesive material 119 positioned on the bottom of the base member 111 so that the deodorant container 10 may be positioned on a vertical surface of secured to a horizontal surface.

The disk 19 of air-treating material may be constructed from a variety of various compositions. The disk 19 may be constructed of a material which would absorb odors, for example, activated charcoal, or may be constructed of a material which would release a fragrance.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A container for a deodorant having first and second housing sections which are telescopically joined together for reciprocal movement with respect to each other between a fully open position and a closed position, air passages being defined between said housing sections in the container open position, said air passages extending into the interior of said container and said air passages being sealed off in the container closed position, the improvement comprising:
   index means for varying the size of said air passages in response to reciprocal movement of said housing sections with respect to each other; and
   locking means for locking said housing sections in said closed position in response to rotation of said housing sections with respect to each other;
   said index means including a plurality of outwardly projecting engaging legs extending from said first housing section and said second housing section.

2. A container according to claim 1, wherein said first housing section includes at least three outwardly projecting engaging legs.

3. A container according to claim 1, wherein said second housing section includes at least three outwardly projecting engaging legs.

4. A container according to claim 1, wherein said plurality of outwardly projecting engaging legs of said first housing include cam blocks positioned on an outer face thereof and are received within slots disposed on an internal surface of said second housing section to permit said first housing to reciprocate into said second housing.

5. A container according to claim 1, wherein said plurality of outwardly projecting engaging legs of said second housing include cam blocks positioned on an outer face thereof and are received within slots disposed on an internal surface of said first housing section to permit said second housing to reciprocate into said first housing.

6. A container according to claim 4 or 5, wherein said first and second housing sections each include at least three outwardly projecting engaging legs spaced apart relative to each other by approximately 120°.

7. A container according to claim 4 or 5, wherein said first and second housing sections each include at least three slots spaced apart by approximately 120°.

8. A container according to claim 7, wherein a disk of air-treating material is disposed within said housing sections and is reciprocated upwardly by disk centering tabs disposed on an inner face of said outwardly projecting legs to raise said disk upwardly as said first housing section is opened relative to said second housing section.

9. A container according to claim 4 or 5, wherein said slots in said first and second housing sections include a vertical portion and said locking means includes a cam slot portion connected to said vertical portion in which said cam blocks of said outwardly projecting engaging legs of said first and second housing sections are operatively positioned to reciprocate within said vertical portion or to be locked within said cam slot portion.

10. A container according to claim 9, wherein said cam blocks of said outwardly projecting engaging legs include detents operatively disposed thereon and are adapted to mate with recesses disposed within said slots of said first and second housing sections to assure the positioning of the first housing in a plurality of open positions relative to the second housing.

11. A container according to claim 1, wherein said first housing section and said second housing section are identical in construction.

12. A container according to claim 1, wherein said first housing section and said second housing section are circular.

13. A container for dispensing an air-treating material comprising:
   a base member including a plurality of outwardly projecting engaging members;
   a top member including a plurality of outwardly projecting engaging members;
   said outwardly projecting engaging members of said base member being operatively, telescopically received by said top member to secure the base members relative to the top member;
   said outwardly projecting engaging members of said top member being operatively, telescopically received by said base member to secure the top member relative to the base member;
   said top member being secured relative to said base member in at least a first position wherein air passages are formed between said top member and said base member and a second position wherein said top member is sealed relative to said base member.

14. A container according to claim 13, wherein said top member includes at least three outwardly projecting engaging members disposed at approximately 120° relative to each other.

15. A container according to claim 13 or 14, wherein said base member includes at least three outwardly projecting engaging members disposed at approximately 120° relative to each other.

16. A container according to claim 15 wherein said outwardly projecting engaging members of said top member and said base member include cam blocks adapted to be received within slots disposed on an internal surface of said base member and said top member, respectively, to permit reciprocal, telescopic movement between said top member and said base member.

17. A container according to claim 16, wherein said top member includes at least three slots disposed at approximately 120° relative to each other.

18. A container according to claim 16, wherein said base member includes at least three slots disposed at approximately 120° relative to each other.

19. A container according to claim 16, wherein said slots in said base member and said top member include a vertical portion and a cam slot portion in which said cam blocks of said outwardly projecting engaging members of said top member and said base member are operatively positioned.

20. A container according to claim 16, wherein said cam blocks of said outwardly projecting engaging members of said top member and said base member include detents operatively disposed thereon and are adapted to mate with recesses disposed within said slots of said base member and said top member, respectively, to assure the positioning of the top member in a plurality of open positions relative to the base member.

21. A container according to claim 19, wherein said top member is closed with respect to said base member when the top member and base member are reciprocated relative to each other and said top member is locked with respect to said base member when the top member is slightly rotated relative to said base member thereby positioning said cam blocks within respective cam slots in said internal surface of said top member and said base member.

22. A container according to claim 13, wherein said top member and said base member are identical in construction.

23. A container according to claim 13, where said outwardly projecting members of said top member and said base member are legs spaced approximately 120° with respect to each other.

24. A container according to claim 13, wherein said top member and said base member are circular members.

25. A container according to claim 13, wherein a disk of air-treating material is disposed within said base member and is reciprocated upwardly by disk centering tabs disposed on an inner face of said outwardly projecting engaging members to raise said disk upwardly as said top member is opened relative to said base member.

26. A container according to claim 25, wherein said disk of air-treating material is centered in said air passages when said container is in a fully opened position.

27. A container according to claim 25, wherein said top member and said base member are identical in construction.

28. A container for a deodorant having a top member and a base member which are telescopically joined together for reciprocal movement with respect to each other between a fully opened position and a closed position, air passages being defined between said top and base members in the container open position, and said air passages being sealed off in the container closed position comprising:

said top member and said base member being identical in construction and being adapted to nest within each other for reciprocal movement between said fully opened and closed positions;

said top member and said base member include outwardly projecting engaging legs having cam blocks adapted to be positioned within corresponding slots disposed within an internal surface of said base member and top member, respectively.

29. A container according to claim 28, wherein said top member and said base member each include at least three outwardly projecting engaging legs spaced apart by approximately 120° and said top member and said base member each include at least three slots spaced apart by approximately 120°.

30. A container according to claim 28, wherein said slots include a vertical portion and a cam slot portion, said cam blocks being reciprocally positioned within said vertical portion of said slots and being locked within said cam slot portion when said top member is slightly rotated relative to said base member.

31. A container according to claim 30, wherein said cam blocks of said outwardly projecting engaging members of said top member and said base member include detents operatively disposed thereon and being adapted to mate with recesses disposed within said slots of said base member and said top member, respectively, to assure the positioning of the top in a plurality of open positions relative to the base member.

32. A container according to claim 28, wherein said top member and said base member are circular members.

33. A container according to claim 28, wherein a disk of air-treating material is disposed within said base member and is reciprocated upwardly by disk centering tabs disposed on an inner face of said outwardly projecting legs to raise said disk upwardly as said top member is opened relative to said base member.

34. A container according to claim 33, wherein said disk of air-treating material is centered in said air passages when said container is in a fully opened position.

35. A container for a deodorant having a top member and a base member which are telescopically joined together for reciprocal movement with respect to each other between a opened position and a closed position, air passages being defined between said top and base members in the container open position, and said air passages being sealed off in the container closed position comprising:

a plurality of outwardly projecting engaging legs disposed on said top member and said base member;

said plurality of outwardly projecting engaging legs including cam blocks positioned on an outer face thereof and being adapted to be positioned within corresponding slots disposed within an internal surface of said base member and top member; and a disk of air-treating material being disposed within said base member and being reciprocated upwardly by disk centering tabs disposed on an inner face of said outwardly projecting legs to raise said disk upwardly as said top member is opened relative to said base member.

36. A container according to claim 35, wherein said disk of air-treating material is centered in said air passages when said container is in a fully opened position.

37. A container according to claim 35, wherein said slots include a vertical portion and a cam slot portion, said cam blocks being reciprocally positioned within said vertical portion of said slots and being locked within said cam slot portion when said top member is slightly rotated relative to said base member.

38. A container according to claim 35, wherein said cam blocks of said outwardly projecting engaging members of said top member and said base member include detents operatively disposed thereon and being adapted to mate with recesses disposed within said slots of said base member and said top member, respectively, to assure the positioning of the top member in a plurality of open positions relative to the base member.

39. A container according to claim 35, wherein said top member and said base member are circular members.

* * * * *